United States Patent
Bloch

(10) Patent No.: US 9,394,557 B2
(45) Date of Patent: *Jul. 19, 2016

(54) LINEAR AMPLIFICATION OF SHORT NUCLEIC ACIDS

(71) Applicant: APPLIED BIOSYSTEMS, LLC, Carlsbad, CA (US)

(72) Inventor: Will Bloch, White Salmon, WA (US)

(73) Assignee: Applied Biosystems, LLC, Carlsbad, CA (US)

(*) Notice: Subject to any disclaimer, the term of this patent is extended or adjusted under 35 U.S.C. 154(b) by 145 days.

This patent is subject to a terminal disclaimer.

(21) Appl. No.: 14/137,786

(22) Filed: Dec. 20, 2013

(65) Prior Publication Data

US 2014/0186893 A1 Jul. 3, 2014

Related U.S. Application Data

(63) Continuation of application No. 13/154,128, filed on Jun. 6, 2011, now Pat. No. 8,628,925, which is a continuation of application No. 12/498,337, filed on Jul. 6, 2009, now abandoned, which is a continuation of application No. 11/421,319, filed on May 31, 2006, now Pat. No. 7,556,943.

(60) Provisional application No. 60/686,384, filed on May 31, 2005.

(51) Int. Cl.
*C12Q 1/68* (2006.01)
*C12P 19/34* (2006.01)

(52) U.S. Cl.
CPC ............... *C12P 19/34* (2013.01); *C12Q 1/6844* (2013.01); *C12Q 1/6853* (2013.01)

(58) Field of Classification Search
None
See application file for complete search history.

(56) References Cited

U.S. PATENT DOCUMENTS

| 5,422,242 | A | 6/1995 | Young et al. | |
| 6,582,938 | B1 | 6/2003 | Su et al. | |
| 7,556,943 | B2 | 7/2009 | Bloch | |
| 8,628,925 | B2 * | 1/2014 | Bloch | 435/6.12 |
| 2009/0269815 | A1 | 10/2009 | Bloch | |

FOREIGN PATENT DOCUMENTS

WO   WO-2005/098029   10/2005

OTHER PUBLICATIONS

Kleter et al., "Development and Clinical Evaluation of a Highly Sensitive PCR-Reverse Hybridization Line Probe Assay for Detection and Identification of Anogenital Human Papillomavirus," Journal of Clinical Microbiology, 1998, vol. 37, No. 8, pp. 2508-2517.*
Liu, et al., "An Oligonucletoide Microchip for Genome-wide microRNA Profiling in Human and Mouse Tissues", *PNAS*,101(26), Jun. 2004, 9740-9744.
PCT/US06/21267, "International Search Report and Written Opinion dated Oct. 19, 2006", 10 Pgs.
Stirewalt, et al., "Single-stranded Linear Amplification Protocol Results in Reproducible and Reliable Microarray Data From Nanogram Amounts of Starting RNA", *Genomics*, 83, 2004, 321-331.

* cited by examiner

*Primary Examiner* — Young J Kim

(57) ABSTRACT

The present teachings provide novel methods for amplifying short nucleic acids. In some embodiments, the present teachings provide novel methods for linearly amplifying a collection of micro RNAs by using temperature cycling during a reverse transcription reaction. The cycling can comprise at least 20 cycles of an annealing temperature segment of 10° C.-30° C., and a denaturation temperature segment of 35° C.-60° C. In some embodiments, the temperature cycled reaction can comprise an osmolyte.

20 Claims, No Drawings

LINEAR AMPLIFICATION OF SHORT NUCLEIC ACIDS

CROSS REFERENCE TO RELATED APPLICATIONS

This application is a continuation of U.S. patent application Ser. No. 13/154,128, filed Jun. 6, 2011, issued as U.S. Pat. No. 8,628,925, which is a continuation of U.S. patent application Ser. No. 12/498,337, filed Jul. 6, 2009, now abandoned, which is a continuation of U.S. patent application Ser. No. 11/421,319, filed May 31, 2006, issued as U.S. Pat. No. 7,556,943, which claims the benefit of priority under 35 U.S.C. §119(e) to U.S. Patent Application No. 60/686,384, filed May 31, 2005, all of which are incorporated herein by reference in their entireties.

FIELD

The present teachings generally relate to methods for amplifying short nucleic acid sequences.

INTRODUCTION

Of the four classes of commonly studied biological macromolecues, nucleic acids have historically proved more amenable to high throughput analyses due in part to the presence of amplification strategies such as PCR. Most of these amplification strategies are inappropriate for proteins, carbohydrates, and lipids. While the central dogma of molecular biology maintains that DNA codes for messenger RNA, which in turn encodes protein, increasing evidence indicates an important role for short RNA molecules such as micro RNAs in regulating gene expression. Due to their short size, amplification procedures such as PCR that are commonly employed for nucleic acids can be difficult to apply to micro RNAs. There is a significant unmet need for methods of amplifying and analyzing short nucleic acids, including micro RNAs.

SUMMARY

In some embodiments, the present teachings provide a method of linearly amplifying a multiplicity of different short nucleic acid sequences, wherein the multiplicity of different short nucleic acid sequences are 15-35 nucleotides in length, said method comprising; forming a reaction mixture comprising a multiplicity of different short nucleic acids, a multiplicity of target-specific primers, and an enzyme that catalyzes target-specific primer extension; annealing the collection of target-specific primers to the multiplicity of different short nucleic acids; extending the multiplicity of target-specific primers with the enzyme that catalyzes target-specific primer extension; cycling the reaction mixture for at least 20 cycles between an annealing temperature segment of 10° C.-30° C., and a denaturation temperature segment of 35° C.-60° C.; and, linearly amplifying the multiplicity of different short nucleic acid sequences.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a primer" means that more than one primer can, but need not, be present; for example but without limitation, one or more copies of a particular first primer species, as well as one or more versions of a particular primer type, for example but not limited to, a multiplicity of different reverse transcription primers. Also, the use of "comprise", "comprises", "comprising", "contain", "contains", "containing", "include", "includes", and "including" are not intended to be limiting.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. In the event that one or more of the incorporated literature and similar materials contradicts this application, including but not limited to defined terms, term usage, described techniques, or the like, this application controls.

SOME DEFINITIONS

As used herein, the term "enzyme that catalyzes target-specific primer extension" refers to any of a variety of enzymes, such as reverse transcriptases, DNA polymerases, etc, which can extend a nucleic acid by addition of dNMPs to its 3' end, thus elongating it.

As used herein, the term "but fails to lose substantial activity" refers to the ability of an enzyme to retain activity over time. For example, an enzyme that retains 90 percent of its original activity after 20 temperature cycles can be said to fail to lose substantial activity. In some embodiments, the enzyme can retain 80 percent of its original activity and be said to fail to lose substantial activity.

As used herein, the term "stem-loop primers" refer to nucleic acids that have a double-stranded stem, a single-stranded loop, and a 3' extendable end that is complementary to a target nucleic acid sequence of interest. Illustrative teachings regarding the use of such stem-loop primers can be found in Chen et al., Nucleic Acids Res. 2005 Nov. 27; 33(20):e179.

As used herein, the term "annealing temperature segment" is used to refer to a low temperature wherein primers can anneal to their corresponding target short nucleic acids. In addition to annealing, extension of the primers can occur during this annealing temperature segment.

As used here, the primers, enzymes, probes, buffers, reaction vessels, and other components will have their customary meaning as appreciated by one of skill in the art of molecular biology. For illustrative teachings see Sambrook and Russell, Molecular Cloning, A Laboratory Manual, 3rd Edition.

EXEMPLARY EMBODIMENTS

Generally, the amplification methods of the present teachings can be considered in light of several observations.

First, the short sequences of micro RNAs have relatively low Tm values. Further, in the context of micro RNAs that have relatively low G:C percentage, strikingly low Tms can be observed.

Second, nucleic acids have high concentration dependences of Tm. As a result of the high concentration dependency of short sequences, the very low concentrations of micro RNAs expected to exist in a single cell/few cell test sample can lower the Tm of a micro RNA for its complementary strand into the near ambient temperature range (e.g.—below 40° C.).

Third, addition of osmolyte (for example betaine, glycerol, sorbitol, etc) to a concentration near two molar in a reverse transcription reaction can have the dually beneficial effect of i) mildly reducing the reverse transcription reaction product Tm, and ii) significantly thermo-stabilizing the reverse transcription enzyme so that it is more likely to survive the mild thermocycling typified in conventional linear reverse transcription reactions. Further, osmolyte can have a third benefit, which is that of iso-stabilizing primer-template duplexes that have different percent G:C. This can have the effect of improving multiplex performance in a manner independent from the aforementioned ability to potentiate thermal cycling.

Fourth, the denaturation time during the reverse transcription thermal cycling can be very short. In some embodiments, the denaturation time can be just a few seconds, even as short as a second. In some embodiments, denaturation times of less than a second are possible. In some embodiments in which a variety of wells in a thermal cycler are being used, the thermal cycling can simply proceed in a manner sufficient to assure that all wells of a thermal cycler reach the desired temperature. This reduced denaturation time can have the effect of further protecting the reverse transcription enzyme, the target RNA template, or the reverse transcription enzyme and the target RNA template, from thermal degradation.

Fifth, short RNA molecules appear to be much more resistant to hydrolytic cleavage, whether RNAse or Mg ion is the dominant catalytic agent, especially as compared with the long mRNA templates of conventional reverse transcription procedures (see for example WO 2004/057017 A2; FIG. 16).

Focusing on the second observation number above, that short sequences such as micro RNAs have high concentration dependences of Tm, provides a surprising and beneficial foundation for a molecular biologist interested in micro RNA profiling. We have observed that the Tm value of any duplex nucleic acid varies in a direct linear manner with the logarithm of molar concentration. Specifically, the Tm value of duplex DNA in the 20 base pair length range drops 2-3° C. for every 90 percent (about one log) reduction in concentration. An example can help illustrate the implications of this observation.

Suppose one is profiling the micro RNAs of one cell in a total reaction volume of 10 microliters. The most highly expressed micro RNA species have about $10^4$ copies per cell. The molar concentration of these $10^4$ copies in a 10 microliter assay volume is $1 \times 10^{-15}$. The Tm of a micro RNA of typical base composition at a 1 micromolar concentration will be around 50° C. With a delta Tm/delta log ° C. of −2.5, the Tm at $1 \times 10^{-15}$ is predicted to be around 27.5° C. That is, 50−(9× 2.5)=27.5. Assuming for this illustration a 3 log target concentration increase because one chooses to analyze 1000 cells instead of 1 cell, the Tm value would still be only 35° C. A micro RNA expressed at the level of about 10 copies per cell would see a Tm value reduced from the previous value by 7.5° C., all other factors being equal. One hundred-fold linear amplification would increase Tm by about 5° C. Given any variety of combinations of expression level, cell number in the test sample, and linear amplification gain, in all likely cases the denaturation temperature range during the reverse transcription thermal cycling will be one which conventional reverse transcriptase enzymes, as well as the labile RNA itself, can tolerate. Such stability of the reverse transcription enzyme and the RNA can be enhanced in those embodiments comprising osmolyte. Further, such stability of the reverse transcription enzyme and the RNA can be enhanced in those embodiments comprising very short denaturation times.

Multiplexed Amplification

Thus, the present teachings provide for efficient multiplexed amplification to produce higher levels of short nucleic acids, including micro RNAs. While many micro RNAs are abundantly expressed and present at levels of thousands to tens of thousands of molecules per cell, other micro RNAs can be quite rare, existing at 1-10 copies per cell. Specifically, the present teachings provide a process for linearly amplifying short nucleic acids such as micro RNA, optionally performed in approximately 2M of a suitable osmolyte such as betaine, sorbitol, glycerol, or combinations thereof, with any of a variety of commercially available reverse transcriptases, comprising around 10-200 thermal cycles with approximately 3 seconds denaturation at a temperature around 40° C. and 1-2 minutes annealing/extension at a temperature around 25° C. The lowest practical Mg concentration can be employed to minimize Mg-catalyzed RNA hydrolysis. This manipulation of Mg concentration can facilitate selection among the reverse transcription enzyme candidates, since different enzymes can have different Mg requirements. Such optimization of Mg concentration is routine in current molecular biology laboratories.

In some embodiments of the present teachings, osmolyte is omitted. In some embodiments of the present teachings, a concentration of less than 2M osmolyte is employed. In some embodiments of the present teachings, a concentration of greater than 2M osmolyte is employed. Typically, a concentration of between 1.5 and 2M osmolyte is employed. In some embodiments of the present teachings, a concentration of 2M osmolyte is employed. Illustrative teachings discussing the benefits of osmolytes in amplification reactions such as PCR can be found in U.S. Pat. No. 6,841,349, U.S. Pat. No. 6,783, 940, and U.S. Pat. No. 6,789,588.

In some embodiments, 100-200 thermal cycles are performed. In some embodiments, greater than 200 cycles are performed. In some embodiments, fewer than 100 cycles are performed. In some embodiments, at least 20 cycles are performed. In some embodiments, 50-250 thermal cycles are performed.

In some embodiments, approximately three second denaturation at a temperature around 40° C., and 1-2 minutes annealing/extension at a temperature around 25° C. are employed. Of course, shorter denaturation times are possible, though typically 3 seconds can provide beneficial precision. Also, longer denaturation times are contemplated by the present teachings, including denaturation times of 4-5 seconds, 5-10 seconds, and 10-60 seconds. Further, denaturation can occur at 40° C., as well as in a variety of nearby temperatures, including 39° C.-41° C., 38° C.-42° C., and 35° C.-45° C. Additionally, the annealing/extension time can be shorter than 1 minute, as well as longer than 2 minutes. Generally, annealing/extension times can be empirically determined to provide for a sufficiently complete reaction. Shorter times than this can result in diminished product yield, and longer times can be wasted time for the experimentalist. Finally, the annealing/extension temperature can be varied by the experimentalist as well, with temperatures ranging from 20° C.-30° C., 22° C.-28° C., and others as can be determined empirically. It will be appreciated that one of skill in the art, armed with the present teachings, can construct a variety of reaction schemes that will fall within the scope of the claimed invention. In those embodiments in which the length of the short nucleic acids reach higher lengths, generally speaking the experimentalist can perform such procedures as increasing the corresponding denaturation temperature, and/or increasing the amount of osmolyte, such procedures serving to offset the increased length of the nucleic acids in such settings.

In some embodiments, at least 50 different short nucleic acid sequences are amplified. In some embodiments, at least 100 different short nucleic acid sequences are amplified. In some embodiments, at least 200 different short nucleic acid sequences are amplified. In some embodiments, at least 300 different short nucleic acid sequences are amplified.

In some embodiments, the collection of different short nucleic acid sequences to be amplified is collected from a sample comprising a single cell. In some embodiments, the collection of different short nucleic acid sequences to be amplified is collected from a sample comprising two cells. In some embodiments, the collection of different short nucleic acid sequences to be amplified is collected from a sample comprising three cells. In some embodiments, the collection of different short nucleic acid sequences to be amplified is collected from a sample comprising five to ten cells. In some embodiments, the collection of different short nucleic acid sequences to be amplified is collected from a sample comprising ten to one hundred cells. In some embodiments, the collection of different short nucleic acid sequences to be amplified is collected from a sample comprising one hundred to one thousand cells. In some embodiments, the collection of different short nucleic acid sequences to be amplified is collected from a sample comprising greater than one thousand cells.

The present teachings can be applied in a number of contexts. For example, in some embodiments the primers employed can be stem-loop primers, as taught for example in U.S. Non-Provisional application Ser. No. 10/947,460 to Chen et al, and Nucleic Acids Res. 2005 Nov. 27; 33(20): e179. In some embodiments, the present teachings can be employed in profiling nucleic acids in small samples, as discussed in co-filed U.S. Non-Provisional Application Methods for Characterizing Cells Using Amplified Micro RNAs claiming priority to U.S. Provisional Applications 60/686, 521 and 60/708,946. In some embodiments, the present teachings can be employed in diagnosing biological conditions such as cancer based on tissue-specific micro RNA markers, as discussed in co-filed U.S. Non-Provisional Application Method for Identifying Medically Important Cell Populations Using Micro RNA as Tissue Specific Biomarkers claiming priority to U.S. Provisional Application 60/686,274. In some embodiments, the amplified micro RNAs can be encoded with sequence information in the reverse primer in the reverse transcription reaction, and downstream singleplex PCR amplification reactions performed to quantify individual micro RNA targets, as taught for example in U.S. Non-Provisional application Ser. No. 11/090,468 and U.S. Non-Provisional application Ser. No. 11/090,830.

Micro RNAs

The short nucleic acids of the present teachings are typically described herein as micro RNAs, though it will be appreciated that any of a variety of nucleic acids can be queried and fall within the scope of the present teachings, including RNA as well as DNA. Generally, the nucleic acids of the present teachings will be between 15-35 nucleotides in length. In some embodiments, the short nucleic acids can be 18-30 nucleotides in length. In some embodiments, the short nucleic acids can be 18-23 nucleotides in length.

5' End Mapping and Characterization

In some embodiments, the methods of the present teachings can be applied to amplify and characterize the 5' ends of nucleic acids, including the 5' end of messenger RNAs. For example, a primer can be hybridized to a target nucleic acid 15-35 nucleotides away from the 5' end of the target. An extension reaction employing an extension enzyme such as a reverse transcriptase can be employed in cycling procedure to result in the linear amplification of the 5' end of the target, since the resulting extension products will be short and will have the benefits described supra for short nucleic acids. Such procedures can be employed to analyze the 5' end of desired target sequences.

Amplification of Cleaved Mutation Sites in Heteroduplex DNA

In some embodiments, the present teachings can be employed to characterize and amplify short nucleic acids that comprise a mutation, and result from for example cleavage of heteroduplex DNA at the mutation site. For example, a variety of mutation detection procedures rely on the cleavage of heteroduplex DNA resulting from a mutation. See for example Published U.S. patent application Ser. No. 09/998,481 regarding Endonuclease V-mediated mutation mapping. Also, regarding various chemical cleavage methods for heteroduplex analysis that could benefit from the amplification and 5' end mapping techniques provided by the present teachings, see for example *Single-nucleotide polymorphism discovery by targeted DNA photocleavage* in PNAS 2004 Sep. 28; 101(39):14040-4. Epub 2004 Sep. 21 to Hart, Johnson, and Barton, as well as U.S. Pat. No. 5,972,618 to Bloch. These procedures can result in the production of short nucleic acids, which can be present in low amounts and in need of amplification. Thus, the short nucleic acids resulting from these and related mutation mapping procedures can be amplified and characterized by the linear amplification methods provided by the present teachings.

Exemplary Reagents Useful in the Present Teachings

| Reagent | Volume (ul) | [Stock] | [Final] | | 3X Mix |
|---|---|---|---|---|---|
| 10X Applied Biosystems cDNA Archiving Kit buffer | 0.5 | 10 | 1 | | 1.5 |
| MMLV Reverse Transcriptase 50 units/ul | .335 | 50 | 3.35 | (3.3 units/ul) | 1.005 |
| 100 mM dNTP | 0.25 | 100 | 5 | (100 mM/ul) | 0.75 |
| Applied Biosystems RNase Inhibitor | 0.065 | 20 | 0.26 | (0.26 units/ul) | 0.195 |
| 192-plex micro RNA stem-loop primers (50 mM) | 0.5 | 50 | 5 | (5 nM) | 1.5 |
| Total RNA 10 ng/ul samples | 3 | 10 | 6 | | 9 |
| dH20 | 0.35 | 0 | 0 | | 1.05 |
| total Volume | 5 | | | | 15 |

Additional teachings regarding various molecular biology approaches, including reverse transcription reactions, as well as general definitions applicable herein, can be found in Sambrook and Russell, Molecular Cloning, A Laboratory Manual, $3^{rd}$ Edition, as well as on the internet.

While the present teachings have been described in terms of these exemplary embodiments, the skilled artisan will readily understand that numerous variations and modifications of these exemplary embodiments are possible without undue experimentation. All such variations and modifications are within the scope of the present teachings. Aspects of the present teachings may be further understood in light of the following claims.

I claim:
1. A method of linearly amplifying a multiplicity of different short nucleic acid sequences, wherein the multiplicity of short nucleic acid sequences are from the 5' ends of a multiplicity of target nucleic acids, said method comprising;

forming a reaction mixture comprising a multiplicity of different target nucleic acids, a collection of target-specific primers, and an enzyme that catalyzes target-specific primer extension, wherein the target-specific primers can hybridize to the target nucleic acids about 15-35 nucleotides away from the 5' end of the target nucleic acids;

annealing the collection of target-specific primers to the multiplicity of target nucleic acids;

extending the multiplicity of target-specific primers with the enzyme that catalyzes target-specific primer extension; and cycling the reaction mixture for at least 20 cycles between an annealing temperature segment of 10° C.-30° C., an extension segment, and a denaturation temperature segment of 35° C.-60° C.;

thereby linearly amplifying the multiplicity of different short nucleic acid sequences.

2. The method according to claim 1 wherein the multiplicity of different target nucleic acids are messenger RNAs.

3. The method according to claim 1 wherein the collection of target-specific primers comprise stem-loop primers.

4. The method according to claim 1 wherein the annealing temperature is 20° C.-30° C.

5. The method according to claim 1 wherein the denaturation temperature is 40° C.-50° C.

6. The method according to claim 1 wherein 20 to 200 cycles are performed.

7. The method according to claim 1 wherein the annealing segment is 1-2 minutes during each cycle.

8. The method according to claim 1 wherein the denaturation segment is 2-10 seconds during each cycle.

9. The method according to claim 1 wherein at least 100 different target nucleic acids are amplified.

10. The method according to claim 1 wherein the reaction mixture comprises an osmolyte.

11. The method according to claim 10 wherein the osmolyte is betaine, sorbitol, or glycerol.

12. The method according to claim 11 wherein the betaine, sorbitol, or glycerol are present in a total concentration of about 2 molar in the reaction mixture.

13. The method according to claim 1 wherein the enzyme that catalyzes target specific primer extension is a reverse transcriptase.

14. The method according to claim 13 wherein the reverse transcriptase is heat-sensitive, but fails to lose substantial activity in the at least 20 cycles.

15. The method according to claim 1 wherein the annealing temperature segment is 20° C.-30° C., the denaturation temperature segment of 40° C.-50° C., and 50 to 250 cycles are performed.

16. A method of linearly amplifying a short nucleic acid sequence from the 5' end of a target nucleic acid molecule, said method comprising;

forming a reaction mixture comprising a target nucleic acid molecule, a target-specific primer, and an enzyme that catalyzes target-specific primer extension, wherein the target-specific primer can hybridize to the target nucleic acid about 15-35 nucleotides away from the 5' end of the target nucleic acid molecule;

annealing the target-specific primer to the target nucleic acid;

extending the target-specific primer with the enzyme that catalyzes target specific primer extension; and cycling the reaction mixture for at least 20 cycles between an annealing temperature segment of 10° C.-30° C., and a denaturation temperature segment of 35° C.-60° C.;

thereby linearly amplifying the short nucleic acid sequence.

17. The method according to claim 16 wherein the annealing temperature segment is 20° C.-30° C., the denaturation temperature segment of 40° C.-50° C., and 50 to 250 cycles are performed.

18. The method according to claim 17 wherein the reaction mixture comprises an osmolyte, and the osmolyte is betaine, sorbitol, or glycerol.

19. The method according to claim 18 wherein the betaine, sorbitol, or glycerol are present in a total concentration of about 2 molar in the reaction mixture.

20. The method according to claim 16 wherein the target nucleic acid molecule is a messenger RNA.

* * * * *